United States Patent [19]

Doctor et al.

[11] Patent Number: 5,695,750

[45] Date of Patent: Dec. 9, 1997

[54] COMPOSITIONS FOR USE TO DEACTIVATE ORGANOPHOSPHATES

[75] Inventors: Bhupandra P. Doctor, Potomac; Donald Maxwell, Baltimore, both of Md.; Ashima Saxena, Fairfax, Va.; Zoran Radic, San Diego; Palmer Taylor, Del Mar, both of Calif.

[73] Assignee: The United States of America as represented by the Secretary of the Army, Washington, D.C.

[21] Appl. No.: 348,920

[22] Filed: Nov. 25, 1994

[51] Int. Cl.⁶ .......................... A61K 38/43; A01N 25/00; C12N 15/00

[52] U.S. Cl. .................. 424/94.1; 424/405; 424/406; 435/172.1

[58] Field of Search .................. 424/94.1, 405, 424/406; 435/172.1

[56] References Cited

U.S. PATENT DOCUMENTS

| | | | |
|---|---|---|---|
| 4,002,760 | 1/1977 | Cook | 424/263 |
| 4,263,305 | 4/1981 | Epstein et al. | 424/263 |

*Primary Examiner*—Michael G. Wityshyn
*Assistant Examiner*—Deborah K. Ware
*Attorney, Agent, or Firm*—John Francis Moran

[57] ABSTRACT

A method of detoxifying organophosphates using mutant cholinesterase which resists aging. The addition of oximes to the cholinesterase further retards aging of the cholinesterase.

3 Claims, 2 Drawing Sheets

FIG. 1

Amino acid sequence of Torpedo AChE

A

```
           10         20         30         40         50         60         70         80         90   *    100        110        120
  1 Torpedo AChE  DDHSELLVNTKSGKVMGTRVPVLSSHISAFLGIPFAEPPVGNMRFRRPEPKKPWSGVWNASTYPNNCQQYVDEQFPGFSGSEMWNPNREMSEDCLYLNIWPSPRPKSTT-VMVWIYG
```

B

```
          130        140        150        160        170        180        190        200    @   210        220        230        240
121 Torpedo AChE  GGFYSGSSTLDVYNGKYLAYTEEVLVSLSYRVGAFGFLALHGSQEAPGNVGLLDQRMALQWVHDNIQFFGGDPKTVTIFGESAGGASVGMHILSPGSRDLFRRAILQSGSPNCPWASVS
```

C

```
          250  260        270                      280        290        300        310        320        330        340        350        360
241 Torpedo AChE  VAEGRRRAVELGRNLNC----NLNSDEELIHCLREKKPQELIDVEWNVLPFDSIFRFSFVPVIDGEFFPTSLESMLNSGNFKKTQILLGVNKDEGSFFLLYGAPGFSKDSESKISREDFM
```

D

```
          370        380        390        400        410        420        430        440    *450        460        470        480
361 Torpedo AChE  SGVKLSVPHANDLGLDAVTLQYTDWMDDNNGIKNRDGLDDIVGDHNVICPLMHFVNKYTKFGNGTYLYFFNHRASNLVWPEWMGVIHGYEIEFVFGLPLVKELNYTAEEEALSRRIMHYW
```

E

```
          490        500        510        520        530        540        550        560        570        580
481 Torpedo AChE  ATFAKTGNPNEPHS-QESKWPLFTTKEQKFIDLNTEPMKVHQRLRVQMCVFWNQFLPKLLNATATIDEAERQWKTEFHRWSSYMHMKNQFDHY-SRHESCAEL
```

FIG. 2

Amino acid sequence of Torpedo $E_{199}Q$ mutant AChE

A

```
    1      10         20         30         40         50         60         70         80      90      100        110        120
Torpedo AChE
    DDHSELLVNTKSGKVMGTRVPVLSSHISAFLGIPFAEPPVGNMRFRRPEPKKPWSGVWNASTYPNNCQQYVDEQFPGFSGSEMWNPNREMSEDCLYLNIWVPSPRKSTT-VMVWIYG
```

B

```
  121        130        140        150        160        170        180        190      200     210        220        230        240
Torpedo AChE
    GGFYSGSSTLDVYNGKYLAYTEEVVLVSLSYRVGAFGFLALHGSQEAPGNVGLLDQRMALQWVHDNIQFFGGDPKTVTIFGQSAGGASVGMHYLSPGSRDLFRRAILQSGSPNCPWASVS
```

C

```
  241        250         260        270        280        290        300        310        320        330        340        350        360
Torpedo AChE
    VAEGRRRAVELGRNLNC----NLNSDEELIHCLREKKPQELIDVEMNVLPFDSIRRFSFVPVIDGEFFPTSLESMLNSGNFKKTQILLGVNKDEGSFLLYGAPGFSKDSESKISREDFM
```

D

```
  361        370        380        390        400        410        420        430        440       450       460        470        480
Torpedo AChE
    SGVKLSVPHANDLGLDAVTLQYTDWMDDNNGIKNRDGLDDIVGDHNVICPLMHFVNKYTKFGNGTYLYFFNHRASNLVWPEWMGVIHGYEIEFVFGLPLVKELNYTAEEEALSRIMHYW
```

E

```
  481        490        500        510        520        530        540        550        560        570        580
Torpedo AChE
    AIFAKTGNPNEPHS-QESKWPLFTTKEQKFIDLNTEPMKVHQRLRVQMCVFWNQFLPKLLNATATIDEAERQWKTEFHRWSSYMMHWKNQFDHY-SRHESCAEL
```

COMPOSITIONS FOR USE TO DEACTIVATE ORGANOPHOSPHATES

FIELD OF THE INVENTION

This invention relates to use of enzymes to detoxify organophosphates using acetylcholinesterase and oximes as a means of treating or preventing deleterious effects from exposure to organophosphates in organisms. The invention also encompasses use of genetically modified acetylcholinesterases to improve effectiveness of the acetylcholinesterase/oxime composition. Abbreviations used are: FBS Ache, fetal bovine serum acetylcholinesterase; OP, organophosphate; HI-6, 1-(2 hydroxyiminomethyl-1-pyridinium)-1-(4-carboxyaminopyridinium) dimethyl ether hydrochloride; SARIN, O-isopropylmethylphosphonofluoridate; PRALIDOXIME CHLORIDE, 2-[hydroxyiminomethyl]-1-methylpyridinium chloride; ChE, cholinesterase; BChE, butyrylcholinesterase; SOMAN, O-pinacolyl methylphosphonofluoridate; MEPQ, 7-(methylethoxyphosphinyloxy)-1-methylquinolinium iodide; TMB$_4$, 1,1-trimethylene bis-(4-hydroximinomethyl) pyridinium dibromide; TABUN, O-ethyl-N,N-dimethyl phosphor-amidocyanidate; VX O-ethyl-S-2-diisopropylaminoethylmethylphosphonothionate; HLo-7, 1-([[4-(aminocarbonyl) pyridino]methoxy]-methyl)-2,4-bis[(hydroxyimino)methyl]-pyridinium dichloride; MMB$_4$, 1,1-methylene-bis-(4-hydroxyiminomethylpyridinium) dibromide.

BACKGROUND OF THE INVENTION

Organophosphates (OP), upon reaction with cholinesterase, produce phosphorylated, phosphonylated, and phosphinylated enzyme conjugates with the active-center serine ($S_{200}$). These conjugates, while relatively slow in turnover, have two dominant modes of reaction. Spontaneous reactivation results from cleavage of the serine-O—P bond forming the reactive serine. Aging results from cleavage of the alkoxy —O—P bond, forming the corresponding P—O$^-$ containing conjugates which can no longer be reactivated. Analysis of the kinetics and Ph profiles of aging suggest two potential mechanisms for aging: a general acid-catalyzed reaction and one catalyzed by a nucleophile/ activated H$_2$O.

The acid or low pH-catalyzed rate of aging appears most rapid with OP-acetylcholinesterase (AChE) conjugates containing tertiary alkoxy groups, followed by secondary and primary alkoxy groups. This suggests that a carbonium ion may serve as an intermediate. Formation of the aged enzyme yields a species resistant to spontaneous or nucleophilic attack to achieve reactivation. This may be due, in part, to the negatively-charged phosphate forming a stable ion pair but may also result from a change in conformation of the conjugated species. Evidence for the former mechanism comes from the crystallographic structure of an aged alkylphosphate-chymotrypsin conjugate, whereas changes in the fluorescence spectra of pyrenebutylphosphono-AChE and chymotrypsin complexes also suggest a change in conformation of the conjugate.

Present treatment for poisoning by organophosphates (OP) consists of a combination of drugs such as carbamates (e.g., pyridostigmine), anti-muscarinic (e.g., atropine), and reactivators (e.g., 2-[hydroxyiminomethyl]-1-methylpyridinium chloride, pralidoxime chloride) administered in post-exposure modalities. Although this drug regimen is effective in protecting experimental animals against lethality by OP poisoning, it is not effective in preventing convulsions, performance deficits, or permanent brain damage. To alleviate these post exposure symptoms, the use of cholinesterases (ChEs) as a pretreatment drug was successfully tested in animals including non-human primates for the sequestration of highly toxic OP anti-ChEs before they reach their physiological targets. For example, pretreatment of rhesus monkeys with FBS AChE or horse serum butyrylcholinesterase protected them against a challenge up to 5 LD$_{50}$ of O-pinacolyl methylphosphonofluoridate (soman), a highly toxic OP. These monkeys pretreated with FBS AChE were devoid of any behavioral incapacitation after soman challenge, as measured by the serial probe recognition task or the primate equilibrium platform performance task. In vivo and in vitro titration of ChEs with a variety of OPs produce a 1:1 stoichiometry between organophosphate inhibited enzymes and the cumulative dose of the toxic nerve agent. These results substantiated the hypothesis that exogenously administered ChEs can effectively sequester in vivo OPs before they reach their physiological targets.

Although the use of cholinesterases as a single pretreatment drug for highly potent OPs is sufficient to provide complete protection without the need for postexposure treatment, its practical use at the present time may be limited. Large quantities of enzymes will be required to provide sufficient protection due to 1:1 stoichiometry (i.e., a single turnover) between OP and enzyme.

Various approaches have been considered for improving the efficacy of ChEs as pretreatment drugs. First, production of catalytic antibodies that hydrolyze OPs. This approach has been attempted. The second approach is the use of hydrolytic enzymes such as OP hydrolases. Parathion hydrolase was shown to hydrolyze tabun with a sufficient rate to be useful as a pretreatment drug but it has a very short half-life in mice.

SUMMARY OF THE INVENTION

It is the purposes of this invention to provide improved means for detoxifying organophosphates by use of a combination of oximes with cholinesterases. In a preferred embodiment of the invention a mutant cholinesterase which is resistent to aging is used. By methods of the invention, it is also possible to provided improved protection of mammals from fatal effects of organophosphates. The use of the methods of the invention provide an environmentally safe method of destroying organophosphates, and avoid the dangers inherent in burning these materials.

BRIEF DESCRIPTION OF THE DRAWINGS

FIG. 1 gives the sequence (SEQ ID NO: 1) of the wild-type Torpedo AChE.

FIG. 2 gives the sequence (SEQ ID NO: 2) for the Torpedo $E_{199}$ mutant AChE.

DETAILED DESCRIPTION OF THE INVENTION

To improve the efficacy of ChEs as pretreatment drugs, an approach was developed in which the catalytic activity of OP-inhibited FBS AChE was rapidly and continuously restored, thus detoxifying the OP and minimizing enzyme aging by having sufficient amounts of appropriate oxime present. The efficacy of FBS AChE to detoxify several OPs was amplified by addition of bis-quaternary oximes, particularly 1-(2-hydroxyiminomethyl-1-pyridinium)-1-(4-carboxyaminopyridinium)-dimethyl ether hydrochloride (HI-6). When mice were pretreated with sufficient amounts of FBS AChE and HI-6 and challenged with repeated doses of O-isopropylmethylphosphonofluoridate (sarin), the OP was continuously detoxified so long as the molar concentration of the sarin dose was less than the molar concentration of AChE in circulation. The in vitro studies showed that the stoichiometry of sarin:FBS AChE in the presence of the oxime was higher than 3200:1 and in vivo stoichiometry with mice was as high as 57:1. Addition of HI-6 to FBS AChE as a pretreatment drug amplified the efficacy of enzyme as a scavenger of nerve agents.

The rate of reactivation of inhibited AChE depends on the source of the enzyme, the specific OP and the oxime used, and its concentration. With irreversible inhibitors such as soman and sarin, the enzyme is inhibited in a relatively short period. Further, in the case of soman, the inhibited enzyme undergoes rapid aging which converts AChE to a non-reactivatible form. Therefore, the immediate administration of an appropriate oxime after OP exposure is extremely important. Thus, the use of a suitable oxime reactivator as a pretreatment drug combined with the exogenous AChE before exposure to an OP regenerates the OP-inhibited enzyme and thereby restores the scavenger's ability to sequester circulating OP.

In studying the reactivation of alkylphosphorylated acetylcholinesterase sarin was evaluated. AChE after alkylphosphorylation by sarin undergoes slow spontaneous reactivation or "aging". The "aged" enzyme is highly resistant to hydrolysis and regeneration by oximes. Oximes such as HI-6 react via a nucleophilic oxime group with electrophilic P atom, forming HI-6-OP-enzyme complex. The oxime phosphonate is split off leaving regenerated enzyme. Slow hydrolysis of oxime-phosphonate complex yields regenerated HI-6 and methyl-isopropyl phosphonate. Rapid inactivation of HI-6 can also occur simultaneously by $\alpha,\beta$, cis-elimination. Studies showed that the addition of HI-6 amplifies the effectiveness of exogenous FBS AChE to detoxify organophosphate not only in vitro but in mice as well. This is possible because the OP-inhibited FBS AChE is reactivated continuously in the presence of HI-6. The selection of HI-6 as reactivator was based on its demonstrated efficacy n protecting animals against OP poisoning.

MATERIALS AND METHODS

Materials: Fetal bovine serum AChE was purified to electrophoretic homogeneity (98% purity) according to De La Hoz et al. (De La Hoz, D. M., B. P. Doctor, J. S. Ralston, R. S. Rush, and A.D. Wolfe. A simplified procedure for the purification of large quantities of fetal bovine serum acetylcholinesterase. *Life Sci.* 39:195–199 (1986). Sarin, soman, O-ethyl N,N-dimethylphosphoramido-cyanidate (tabun) and O-ethyl S-2-diisopropylaminoethyl methylphosphonothionate (VX) were obtained from the Chemical Research, Development, and Engineering Center (Aberdeen Proving Ground, Md.). Acetylthiocholine (ATC), and bovine serum albumin (BSA) were purchased from Sigma Chemical Co. (St. Louis, Mo.). HI-6, 1-([[4-(aminocarbonyl)pyridino]-methoxy]-methyl)-2,4-bis[(hydroxyimino)methyl] pyridinium dichloride (HLo-7), 1,1-methylene-bis(4-hydroxyimino-methylpyridinium) dibromide (MMB$_4$), TMB$_4$ and pralidoxime chloride were obtained from the Division of Experimental Therapeutics, Walter Reed Army Institute of Research, Washington, D.C. Human plasma was obtained from out-dated human blood provided by Camp Memorial Blood Center, Fort Knox, Ky. Plasma was centrifuged at 105,000 g for 1 hr and aliquots frozen at $-20°$ until used.

AChE Assay: AChE activity was determined by the spectrophotometric method of Ellman et al. (Ellman, G. L., K. D. Courtney, Featherstone B. M. Andres. A new and rapid colorimetric determination of acetylcholinesterase activity. *Biochem. Pharmacol.* 7:88–95 (1961)) with 0.5 mM ATC as the substrate. The AChE level of mouse blood was determined after at least a 10-fold dilution in distilled water. The assays were conducted in 50 mM phosphate buffer, pH 8.0 at 25°.

Determination of Sarin or Soman Potency: The potency of sarin or soman solutions to be used for the study experiments was determined by (a) titrating with a known amount of FBS AChE and (b) determination of $LD_{50}$ in mice.

In Vitro Titration of FBS AChE With OP Compounds: Serial dilutions of OP in saline were incubated with 0.1 µM AChE at room temperature for at least 30 min in 50 mM phosphate buffer, pH 8.0 with and without the presence of human plasma. Residual AChE activity was plotted against the concentration of OP added to the reaction mixture to indicate the stoichiometry between AChE and OP.

Determination of i.v. $LD_{50}$ of Sarin: The i.v. $LD_{50}$ of sarin in mice was determined and calculated by the method of Spearman-Kerber (Finney, D. J. The Spearman-Karber Method, in *Statistical Methods in Biological Assay*, (D. J. Finney, ed.) Charles Griffin, London, 542–530 (1964)). The $LD_{50}$ of sarin was also determined in mice pretreated with 50 mg/kg HI-6 (5 min before bolus injection of sarin). The survivability tests were carried out with (a) mice pretreated with 8–9 nmol of FBS AChE (1 hr before bolus injection of sarin) and (b) with 8–9 nmol of FBS AChE and 50 mg/kg HI-6.

Effect of Mixing HI-6 with Sarin on its Ability to Inhibit FBS AChE: One mM sarin and 1 mM sarin+1 mM HI-6 mixture were incubated at 25° for 1 and 2 hr. Appropriate amounts of both of these solutions were diluted to a final concentration of 12 nM each into approximately 13 nM of FBS AChE with 0.01% BSA. The extent of dilution of both these solutions was such that the inhibitory ability of sarin would be approximately 75%. Indeed, this theoretical value was found to be in reasonable agreement with the observed values which was determined after a 0.5 hr incubation period. It should be pointed out that the concentration of HI-6 (12 nM) in the diluted solution did not cause any significant reactivation of sarin-inhibited FBS AChE over a 30 minute incubation period.

Kinetics of Reactivation of OP-inhibited FBS AChE: Inhibition of FBS AChE (0.1 µM) was performed in 50 mM phosphate pH 8.0 at 25° with aqueous solutions of sarin or soman (1 µM). The AChE activity in the reaction mixture was measured after a 10 min incubation to confirm that greater than 95% inhibition of AChE had occurred. The OP-inhibited AChE was then separated from excess inhibitor by high performance liquid chromatography on a TSK-SW2000 gel filtration column equilibrated with phosphate buffer. Each OP-inhibited AChE sample was compared to a corresponding control AChE sample which had received identical incubation and chromatography treatment except for the absence of OP inhibitor. After chromatographic separation the sample of OP inhibited AChE was reactivated at 25° by addition of 2 mM HI-6 in 50 mM phosphate, pH 8.0. Samples (10 µl) of the reaction mixture were assayed (300× dilution in Ellman reagent) sequentially for AChE activity at intervals up to one hour. The observed constant ($K_{obs}$) for the oxime reactivation of OP inhibited AChE was calculated from the equation $v=V_{max}(1-e^{-k_{obs}t})$ where $V_{max}$ was the maximal recovery of AChE activity and v is the activity at any given time (t). Since the reactivation and aging of OP-inhibited enzymes are parallel first-order reactions, the true rate constants were calculated according to the method of Hovanec and Lieske (Hovanec, J. W., and C. N. Lieske. Spontaneous reactivation of acetylcholinesterase inhibited with para-substituted phenylmethylphosphono chloridates. *Biochemistry* 11:1051–1056 (1972)). Under the experimental conditions described above, the final concentration of HI-6 in the assay mixture did not affect the rate of the non-specific hydrolysis of AChE, nor the activity of AChE.

In Vitro Detoxification of OPs: The incubation mixture in 50 mM phosphate buffer, pH 8.0 (total volume 0.5 ml) contained 0.35 ml human plasma, 0.1–0.15 μM FBS AChE, 1–10 mM oxime and variable concentrations of OP compounds. Residual enzyme activity was determined after incubation at room temperature for different intervals of time. Two protocols were used: (A) various concentrations of OP were added at t=0 to the reaction mixture to constitute different OP/AChE molar concentrations. At different time intervals, residual activity of AChE was assayed by diluting the reaction mixture 300-fold into the assay cuvette; (B) to a series of reaction mixtures, equal amounts of OP were added at t=0. After 0.5 hr, the first reaction mixture was discarded after its residual activity was determined. To each of the remaining reaction mixtures the same amount of OP was added and enzyme activity was determined in the second tube after another 0.5 hr. The process of repeated additions of OP to the subsequent mixtures, was designed to simulate multiple OP exposure in vivo. This procedure was repeated numerous times until the enzyme activity decreased to 10% of its original value. Residual enzyme activity was plotted against the cumulative concentration of the OP added to each reaction mixture to indicate the ratio of hydrolyzed OP against given enzyme concentration.

In Vivo Reactivation of Sarin-Inhibited FBS AChE by HI-6 in Mice: In one series of experiments, mice (n=5) were injected i.v. with approximately 4,000 units (10 nmol active site) of FBS AChE. One hour later, blood was withdrawn for AChE determination. Each mouse was then injected i.v. with a freshly prepared mixture of 2 μg (14.3 nmol) of sarin and 1 mg HI-6 (2.6 μmol) followed 15 min later by blood withdrawal and AChE determination. Five additional sarin/HI-6 mixtures were injected into each mouse and blood samples withdrawn 15 min after each injection for AChE determination. In a second series of experiments, mice were pretreated with FBS AChE (3,500 units/mouse) 1 hr before the initiation of the titration experiment. HI-6 (50 mg/kg; 3.2 μmol) were injected i.v. 5 min before the first i.v. administration of 2.6 μg of sarin/mouse. The subsequent four sarin injections did not contain HI-6.

Study of an aging-resistant AChE: Wild type and $E_{199}Q$ mutant of Torpedo AChE were expressed and purified by affinity chromatography. One nmole of wild type AChE was equivalent to 250 units, and one nmole of $E_{199}Q$ mutant AChE was equivalent to 42 units. Soman was obtained from the Chemical Research, Development and Engineering Center (Aberdeen Proving Ground, Md.). Soman used in these experiments was 98.6% pure when analyzed by [$^{31}$P] nuclear magnetic resonance. Concentrations of soman solutions were determined by titration of the solution with a known amount of fetal bovine serum (FBS) AChE and measurement of residual activity (1 nmol of FBS AChE is equivalent to 400 units). The oxime, 1-(2-hydroxyiminomethyl-1-pyridinium)-1-(4-carboxyaminopyridimium)-dimethyl ether hydrochloride (HI-6), was obtained from the Division of Experimental Therapeutics, Walter Reed Army Institute of Research.

Titration of AChE With Soman. Dilutions of soman in saline were incubated with AChE at room temperature for at least 30 min in 50 mM sodium phosphate, pH 8.0, containing 0.01% BSA. Residual AChE activity was plotted against the concentration of soman added to the reaction mixture to ascertain the stoichiometry between AChE and soman.

Time Course for the Reactivation of Soman-Inhibited AChE with HI-6: Fifty μl aliquots of enzyme (0.8 units/ml, 50 mM phosphate, pH 8.0, containing 0.01% BSA) were incubated at room temperature with various amounts of soman for 30 min; 5 μl was withdrawn for assay of residual AChE activity using the Ellman method (Ellman, G. L., Courtney, K. D., Andres, V., Jr., and Featherstone, R. M. (1961) Biochem. Pharmacol. 7, 88–95). To the remaining sample, 3 μl of 40 mM HI-6 solution was added so that the final concentration of oxime was 2.5 mM. Enzyme activity of aliquots of the reactivation mixture were measured at intervals of 0.5, 1, 2, 3, 4, 6, and 24 hr using the Ellman method.

pH Profile for the Aging of AChE: To 108 μl of AChE (0.9 units/ml) were added 12 μl of one of the 0.5M buffer stock solutions at different pH values. The following buffer solutions were used: sodium acetate at pH 5.0 and 5.5; sodium phosphate at pH 6.0, 6.5, 7.0, 7.5, and 8.0; Tris-HCl at pH 8.5. For each pH, soman was mixed with enzyme at concentrations of 3 ng/ml for wild type AChE and 60 ng/ml for $E_{199}Q$ mutant AChE. These concentrations of soman were slightly in excess of the amounts needed to completely inhibit the wild type and mutant AChE. Parallel samples without soman were used to monitor stability of the enzyme at each pH. Ten μl aliquots were removed at various time intervals and transferred to tubes containing 10 μl of 5 mM HI-6 in 50 mM phosphate, pH 8.0. Samples were incubated overnight at room temperature before assay for AChE activity using the Ellman method.

It had been reported that some OPs react to form phosphorylated oximes which are potent inhibitors of AChE. To test this possibility, sarin and HI-6 were preincubated for 1 and 2 hr at 25°, and diluted to greater than 10,000-fold. This mixture was used to test the ability of sarin to inhibit FBS AChE. As shown in Table 1, the ability of sarin to inhibit FBS AChE was not changed by incubating it with HI-6 at room temperature for up to 2 hr as compared to sarin incubated under the same conditions without HI-6.

TABLE 1

EFFECT OF MIXING HI-6 WITH SARIN ON ITS ABILITY TO INHIBIT FBS AChE

| ADDITION | INCUBATION TIME (HOURS) | | |
|---|---|---|---|
| | 0 | 1 | 2 |
| | AChE, U/ML % | | |
| NONE | 3.71 ± 0.21 (100) | 3.71 ± 0.21 (100) | 3.71 ± 0.21 (100) |
| SARIN | 0.93 ± 0.21 (25.13 ± 4.27) | 0.88 ± 0.11 (23.87 ± 4.62) | 0.87 ± 0.14 (23.44 ± 4.34) |
| SARIN + HI-6 | 0.82 ± 0.12 (22.25 ± 4.43) | 0.83 ± 0.13 (22.35 ± 4.01) | 0.83 ± 0.14 (22.38 ± 4.20) |

Each data point represents the average of AChE assays on five samples.

The effect of titration of FBS AChE by MEPQ in the presence or absence of HI-6 were studied in vitro. The titration was carried out in the presence of 70% human plasma in 50 mM phosphate buffer, pH 8.0, in order to mimic the physiological conditions. As expected 1:1 stoichiometry between FBS AChE and MEPQ was observed. The rate of reactivation of MEPQ-inhibited FBS AChE under these experimental conditions depends on the molar concentration of oxime. In all cases more than 90% of the enzyme activity was restored after 160 min. This amount corresponds to the hydrolysis of approximately one nmol of MEPQ by a mixture of 0.037 nmol of FBS AChE and 2 mM HI-6. Repeated additions of MEPQ to FBS AChE in presence of HI-6 at one-half hour intervals appears to continuously reactivate the enzyme. All the added MEPQ was destroyed. This conclusion was based on the observation that the addition of an aliquot of the last reaction mixture to fresh FBS AChE solution (containing no HI-6) did not show any enzyme inhibition. The incubation mixture contained 0.7 ml human plasma, FBS AChE (37 units; 0.095 nmol), and increasing amounts of MEPQ in a final volume of 1 ml (50 mM phosphate buffer, pH 8.0). The mixture was incubated at room temperature for 1 hr and the residual AChE activity was measured by Ellman method.

The results of the in vitro titration of FBS AChE by sarin, in presence and absence of 2 mM HI-6 was also studied. Since only the (P-) of the two enantiomers of sarin has been shown to inhibit AChE, twice the molar concentration of a racemic mixture of sarin was required to completely inhibit molar amount of the enzyme. Greater than stoichiometric amounts of sarin did not inhibit FBS AChE in presence of 2 mM HI-6. Repeated addition of ten times the molar concentration of sarin to FBS AChE in presence of 2 mM HI-6 every one-half hr (total of 10 times) did not result in any inhibition of the enzyme. A total of 28.8 nmol of sarin was neutralized by 0.144 nmol of FBS AChE in presence of 2 mM HI-6 (approximately 100 times more than the expected amount) without any loss of enzyme activity. This continuous neutralization of sarin is further evident when progressively larger molar excesses of sarin were added to FBS AChE in the presence of HI-6. Inhibition of enzyme activity was observed only when the total amount of sarin exceeded the molar concentration of enzyme by greater than 3200. All of the cumulative sarin added to the reaction mixture was completely neutralized, since an aliquot of this reaction mixture taken after the last sarin addition did not inhibit fresh enzyme solution without HI-6.

To evaluate the kinetics of sarin neutralization by a single cycle of HI-6 reactivation, FBS AChE was inhibited with an excess of sarin, separated from free sarin on HPLC, and reactivated with HI-6. Sarin-inhibited AChE was almost completely reactivated by 2 mM HI-6 in 10 min with a first-order rate constant of 0.35 min$^{-1}$. This suggests that the half-life for AChE reactivation is approximately 2 min and that HI-6 reactivation enables FBS AChE to detoxify one-half its molar equivalent of sarin every 2 min under these experimental conditions.

The in vitro titration of FBS AChE by soman in the absence and presence of 1 mM HI-6 was studied. Addition of 0.33 nmol of soman to the reaction mixture containing 0.14 nmol of FBS AChE completely inhibited enzyme activity in the absence of HI-6 (the extrapolated amount of soman needed to completely inhibit this amount of enzyme would be 0.276 nmol), whereas only 17% (0.024 nmol) of the AChE activity was inhibited in presence of 1 mM HI-6. Under these experimental conditions the amount of soman needed to inhibit 100% enzyme activity in the presence of HI-6 will require approximately 2 nmol. Thus, the same amount of FBS AChE is able to neutralize 7.2 times more soman in presence of 1 mM HI-6 (2.0/0.275=7.2) than in absence of HI-6.

The concentration of HI-6 was increased to 2 mM and the amount of soman added to reaction mixture was lowered to less than the amount required to inhibit all of the FBS AChE. The results showed that FBS AChE (0.144 nmol) in the presence of 2 mM HI-6 continued to neutralize repetitive additions of soman (0.22 nmol) as long as the soman concentration did not exceed the concentration of FBS AChE during the incubation period. Enzyme activity was determined before each addition of soman (30 min).

To evaluate the kinetics of soman neutralization by a single cycle of HI-6 reactivation, FBS AChE was inhibited by an excess of soman, separated from soman on HPLC, and reactivated with HI-6 as previously described for sarin. The kinetics of HI-6 reactivation of soman-inhibited AChE differed from sarin-inhibited AChE both in the extent of reactivation and the rate constant for reactivation. Only 48% of the soman-inhibited AChE was reactivated, presumably because of aging that occurred during the approximately 10 min required to inhibit and separate free inhibitor from inhibited enzyme by HPLC. The apparent rate constant for reactivation by 2 mM HI-6 was 0.075 min$^{-1}$ which was 4.7 times less than that for HI-6 reactivation of sarin-inhibited FBS AChE. This rate constant suggests that, under these conditions, the half-life for AChE reactivation is 9.2 min and that HI-6 reactivation enables FBS AChE to detoxify one-half its molar equivalent of soman every 9.2 min. Recently HLo-7, another bis-quaternary oxime, was shown to be equally as effective antidote against soman toxicity as HI-6. Therefore, 1,2, and 5 mM HLo-7 were tested and compared with the same concentrations of HI-6 to determine their ability to reactivate soman-inhibited FBS AChE. It was shown that the oxime, HLo-7, is a better reactivator of soman inhibited FBS AChE than HI-6 at the 1 or 2 mM concentration. Both oximes are equally effective as reactivators at the 5 mM concentration.

Other oximes, such as pralidoxime chloride, TMB$_4$, and MMB$_4$ are also effective in reactivating OP-inhibited FBS AChE. The results of the effectiveness of these oximes for reactivation of the four OP-inhibited FBS AChE are described in Table 2. With 2 mM concentration of HI-6, the activity of all four OP inhibited FBS AChE was almost completely restored. The rank order of the effectiveness of these four oximes against soman toxicity was HI-6>MMB$_4$>pralidoxime chloride>TMB$_4$, against Tabun was HI-6>TMB$_4$>pralidoxime chloride>MMB$_4$, and against VX was HI-6>MMB$_4$=pralidoxime chloride>TMB$_4$. All oximes were equally effective against sarin at 2 mM concentration.

TABLE 2

IN VITRO REACTIVATION OF OP INHIBITED FBS ACHE BY OXIMES

| OXIME mM | SOMAN* | SARIN* | TABUN* | VX* |
|---|---|---|---|---|
| | | AChE ACTIVITY, % | | |
| TMB$_4$ | | | | |
| 0 | 0.0 | 1.1 ± 0.2 | 52.0 ± 3.5 | 0.0 |
| 2 | 20.7 ± | 93.4 ± | | 86.9 ± |
| Pralidoxime chloride | | | | |
| 0 | 0.0 | 1.1 ± 0.2 | 52.0 ± | 0.0 |
| MMB$_4$ | | | | |
| 0 | 0.0 | 1.1 ± 0.2 | 52.0 ± 3.5 | 0.0 |
| 2 | 54.3 ± | 100 | | 95.0 ± |
| HI-6 | | | | |
| 0 | 0.0 | 1.1 ± 0.2 | 52.0 ± 3.5 | 0.0 |
| 2 | 94.5 ± | 98.8 ± | | 97.4 ± |

(*amount used was 150 ng/ml)

46 u/ml FBS AChE, 0.35 ml plasma in 50 mM phosphate buffer pH 8.0, (final volume 0.5 ml) were incubated with and without 2 mM oximes and OPs for 4 hr at room temperature.

The residual AChE activity was determined by Ellman Assay. Each data point represents the average of duplicate AChE assays on five samples.

In Vivo Reactivation of Sarin-Inhibited FBS AChE by HI-6

To determine the effectiveness of HI-6 for in vivo reactivation of sarin inhibited exogenously administered FBS AChE in mice, a mixture of sarin and HI-6 was injected i.v., repeatedly (five or six times) every 15 minutes, to a group (n=5) of mice 1 hour after i.v. administration of FBS AChE. The blood AChE levels were determined before each sarin+ HI-6 injection. The results described in FIG. 7A show the in vivo reactivation of sarin-inhibited FBS AChE by HI-6 in mice. Approximately 7–8 nmols of enzyme were present in the circulation of each mouse before the start of sarin+HI-6 injections. One nmol of (400 units=1 nmol) is inhibited by 280 ng (2 nmols of racemic mixture) of sarin in the absence of HI-6. Based on in vitro titrations, to inhibit the 7–8 nmols of FBS AChE, 14–16 nmols (1.96–2.24 μg) of sarin would be required. The average decrease in blood AChE level per each μg of sarin injected with HI-6 was approximately 25 units as compared to 1450 units per μg of sarin without HI-6 (see in vitro data). Thus, the stoichiometry of AChE:sarin in vivo was enhanced 57-fold in the presence of HI-6 in the i.v. injected challenge. Since the half-life of HI-6 in rodents is relatively shorter than FBS AChE (approximately a factor of 1:60), the repeated sarin doses also contained HI-6 so that a constant level of HI-6 is maintained for reactivation of sarin-inhibited FBS AChE in mice blood.

The average decrease in blood AChE level per each μg of sarin injected after a single HI-6 pretreatment was approximately 115 units as compared to 25 units/μg with multiple HI-6 administration and 1450 units/μg of sarin without HI-6. The stoichiometry of AChE:sarin in these in vivo experiments was 1:12 with single administration of HI-6. These results show that an adequate amount of oxime reactivator is required to continuously reactivate the in vivo sarin-inhibited FBS AChE The detoxification of organophosphates using cholinesterases may, therefore, be accomplished by adding a mixture of at least one oxime and a cholinesterase to the organophosphate. The ratio of 400 to 8000 moles oxime per mole of cholinesterase is preferred. The large excess of oxime is required because of the short half-life of the oxime.

In the intact animal, the administration of a protective dose of exogenous ChE followed by repeated doses of oxime can prove to be effective as a means of protecting against the untoward effects of exposure to organophosphates. A preferred dosage is cholinesterase at about 1 mg/Kg and oxime of about 8 mg/Kg of body weight. The cholinesterase/oxime would be administered in pharmaceutically acceptable buffers before exposure to organophosphates. Persons particularly in need of such prophylactic treatment include any workers that might be exposed to organophosphates. This is particularly important when individuals are charged with destruction of large amounts of organophosphates.

Use of the mutant AChE:

The kinetics of aging in a pinacolylmethylphosphonofluoridate (soman)-inhibited mutant enzyme in which the glutamate ($E_{199}$) located at the amino-terminal to the active-site serine ($S_{200}$) was converted to glutamine (Q). For wild type enzyme, the soman-acetylcholinesterase conjugate aged immediately, giving rise to a form of enzyme resistant to reactivation by oximes. In contrast, the $E_{199}$Q mutant enzyme was largely resistant to aging and could be reactivated by oximes. Since the pH dependence for aging was not altered appreciably, the primary influence of the loss of charge appears to be on the intrinsic rate of aging. The negative charge on $E_{199}$ likely imparts an inductive effect on the conjugated organophosphate to facilitate removal of the alkoxy group. The mutated gene for the AChE of *Torpedo californica* was expressed in baculovirus. The baculovirus is being deposited in the ATCC.

Using the mutant AChE (SEQ ID NO: 2) shown in FIG. 2 resulted in a constantly renewing AChE. Hence, an important aspect of this invention is the use of mutant AChE with oxime for improved long-term effects. The dosage administered was the same as listed above in the general case, namely, 8 mg/Kg oxime and 1 mg/Kg. AChE. The half-life of AChE is about 40 hours. A composition containing 8 mg/Kg oxime and 1 mg/kg AChE would protect for about 40 hours, because the AChE would be resistent to aging. Comparison of the mutant with the natural oxime of Torpedo AChE was studied as indicated below.

Alkylphosphates react more slowly with the $E_{199}$Q mutant than wild type AChE. For example, in the mutant enzyme, diisopropylfluorophosphate and haloxon showed 263-fold and 50-fold reductions in the rate of phosphorylation. In contrast, reductions in the rates of sulfonylation and carbamoylation in the mutant enzyme appear to be smaller (5-fold and 3- to 20-fold, respectively). In the case of carbamoylating substrate, this mutation had little effect on deacylation rates. After phosphorylation with haloxon, appreciable spontaneous reactivation was not evident in the wild type and mutant enzymes.

The crystal structure of the Torpedo AChE shows $E_{199}$ to reside at the base of the active-center gorge, and its electron cloud appears to reside within 1.5 Å of that of the quaternary ammonium group of the substrate or inhibitor bound to the active center of the enzyme.

Using $E_{199}$ soman-inhibited AChE was studied. In this instance, the rate of aging is sufficiently rapid that it occurs concomitantly with the inactivation of enzyme. At the concentrations of soman employed, the approach to inhibition appeared practically stoichiometric, and the differences in titration curves reflect the 6-fold difference in $k_{cat}$ for acetylthiocholine hydrolysis between wild type and mutant enzymes. It was found that only the mutant enzyme was reactivated by the oxime HI-6 at pH 8.0. At least 85% of the wild type enzyme had aged prior to addition of HI-6. In contrast, reactivation of the $E_{199}$Q mutant enzyme was rapid and virtually complete, and the presence of excess soman had little influence on the reactivation rate.

Aging has been proposed to occur by two mechanisms: a pH-dependent, proton-catalyzed dealkylation via a carbonium-ion intermediate and an enzyme or base-catalyzed hydrolytic cleavage. Since the first mechanism shows an increased rate of aging at low pH, the pH dependence of aging was studied by incubation of the enzyme-soman conjugate at various pH's and subsequent measurement of the extent of reactivation by HI-6 at pH 8.0. In general, the aging constants fop $E_{199}$Q mutant AChE were 150–700 fold lower at pH 7.0–7.5 than wild type AChE. At pH values below 7.5, aging of the wild type enzyme was too rapid to measure the aging constants accurately. At pH 8.0 and above, the rate of aging of $E_{199}$Q mutant was so slow that it could not be measured under present experimental conditions (Table 3). The soman-$E_{199}$Q mutant enzyme conjugate showed essentially no aging after 24 hour incubation at pH 8.0.

TABLE 3

PH DEPENDENCE OF THE RATE CONSTANTS FOR THE AGING OF TORPEDO WILD TYPE AND $E_{199}Q$ MUTANT ACETYLCHOLINESTERASES

| pH | $k^\dagger(min^{-1})$ Wild Type | $E_{199}Q$ |
|---|---|---|
| 5.5 | 0.14 ± 0.02‡ | 0.0008 ± 0.0002 |
| 6.0 | 0.34 ± 0.04‡ | 0.0200 ± 0.0020 |
| 6.5 | 0.37 ± 0.07‡ | 0.0050 ± 0.0010 |
| 7.0 | 0.15 ± 0.06‡ | 0.0010 ± 0.0002 |
| 7.5 | 0.18 ± 0.03 | 0.0003 ± 0.0001 |
| 8.0 | 0.08 ± 0.03 | ND |
| 8.5 | 0.05 ± 0.01 | ND |

†Determined by non-linear regression analyses of kinetic data shown in Fig. 3.
‡Estimates from the residual portion of the kinetic profiles (FIG. 3).
ND:Aging not detected over a 24-hr period.

Although the rates of aging differ greatly, wild type and mutant enzymes show an increase in the rate of aging with decreasing pH (Table 3). A similar pH dependence for the soman-Electrophorus AChE conjugate was observed previously. This overall profile for both enzymes is consistent with an aging mechanism involving a carbonium-ion intermediate. The small decrease in the rate of aging of $E_{199}Q$ at pH 5.5 may reflect partial unfolding or a different conformational state of the enzyme. Irreversible denaturation of enzyme is known to occur at this and lower pH values.

Similar pH dependencies suggest that aging in both enzyme conjugates is occurring by a common mechanism. Data also suggest that the carboxylate anion does not serve as attacking nucleophile in aging. It may be involved in influencing polarity of the phosphorus-oxygen dipole or stabilization of the carbonium ion intermediate in the aging reaction. The carboxylate side chain of $E_{199}$ may reside near the effective positive charge on the phosphorus-oxygen dipole, thereby facilitating proton addition. Alternatively, it may ion pair with and effectively facilitate carbonium ion formation on the corresponding carbon of the pinacolyl moiety.

Aging has proven to be the major barrier to achieving oxime reactivation of AChE inhibited by the more potent organophosphates. Recombinant enzymes without this liability would confer a superior characteristic in the development of catalytic scavengers of organophosphates.

We claim:

1. A mutant cholinesterase (AChE) which is Torpedo $E_{199}Q$ mutant AChE having the amino acid sequence of FIG. 2 (SEQ ID NO: 2).

2. A composition of matter comprising the cholinesterase of claim 1 and an oxime.

3. The composition of claim 2 further comprising an organophosphate.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 575 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:1:

```
Asp  Asp  His  Ser  Glu  Leu  Leu  Val  Asn  Thr  Lys  Ser  Gly  Lys  Val  Met
  1              5                         10                       15

Gly  Thr  Arg  Val  Pro  Val  Leu  Ser  Ser  His  Ile  Ser  Ala  Phe  Leu  Gly
                20                        25                       30

Ile  Pro  Phe  Ala  Glu  Pro  Pro  Val  Gly  Asn  Met  Arg  Phe  Arg  Arg  Pro
           35                        40                       45

Glu  Pro  Lys  Lys  Pro  Trp  Ser  Gly  Val  Trp  Asn  Ala  Ser  Thr  Tyr  Pro
      50                        55                       60
```

```
Asn  Asn  Cys  Gln  Gln  Tyr  Val  Asp  Glu  Gln  Phe  Pro  Gly  Phe  Ser  Gly
 65                      70                      75                       80

Ser  Glu  Met  Trp  Asn  Pro  Asn  Arg  Glu  Met  Ser  Glu  Asp  Cys  Leu  Tyr
                85                       90                            95

Leu  Asn  Ile  Trp  Val  Pro  Ser  Pro  Arg  Pro  Lys  Ser  Thr  Thr  Val  Met
               100                      105                     110

Val  Trp  Ile  Tyr  Gly  Gly  Gly  Phe  Tyr  Ser  Gly  Ser  Ser  Thr  Leu  Asp
          115                      120                      125

Val  Tyr  Asn  Gly  Lys  Tyr  Leu  Ala  Tyr  Thr  Glu  Glu  Val  Val  Leu  Val
     130                      135                     140

Ser  Leu  Ser  Tyr  Arg  Val  Gly  Ala  Phe  Gly  Phe  Leu  Ala  Leu  His  Gly
145                      150                      155                           160

Ser  Gln  Glu  Ala  Pro  Gly  Asn  Val  Gly  Leu  Leu  Asp  Gln  Arg  Met  Ala
                165                           170                     175

Leu  Gln  Trp  Val  His  Asp  Asn  Ile  Gln  Phe  Phe  Gly  Gly  Asp  Pro  Lys
               180                      185                          190

Thr  Val  Thr  Ile  Phe  Gly  Glu  Ser  Ala  Gly  Gly  Ala  Ser  Val  Gly  Met
               195                      200                     205

His  Ile  Leu  Ser  Pro  Gly  Ser  Arg  Asp  Leu  Phe  Arg  Arg  Ala  Ile  Leu
     210                      215                      220

Gln  Ser  Gly  Ser  Pro  Asn  Cys  Pro  Trp  Ala  Ser  Val  Ser  Val  Ala  Glu
225                      230                      235                           240

Gly  Arg  Arg  Arg  Ala  Val  Glu  Leu  Gly  Arg  Asn  Leu  Asn  Cys  Asn  Leu
                245                      250                          255

Asn  Ser  Asp  Glu  Glu  Leu  Ile  His  Cys  Leu  Arg  Glu  Lys  Lys  Pro  Gln
               260                      265                     270

Glu  Leu  Ile  Asp  Val  Glu  Trp  Asn  Val  Leu  Pro  Phe  Asp  Ser  Ile  Phe
          275                      280                     285

Arg  Phe  Ser  Phe  Val  Pro  Val  Ile  Asp  Gly  Glu  Phe  Phe  Pro  Thr  Ser
     290                      295                     300

Leu  Glu  Ser  Met  Leu  Asn  Ser  Gly  Asn  Phe  Lys  Lys  Thr  Gln  Ile  Leu
305                      310                      315                           320

Leu  Gly  Val  Asn  Lys  Asp  Glu  Gly  Ser  Phe  Phe  Leu  Leu  Tyr  Gly  Ala
               325                      330                          335

Pro  Gly  Phe  Ser  Lys  Asp  Ser  Glu  Ser  Lys  Ile  Ser  Arg  Glu  Asp  Phe
               340                      345                     350

Met  Ser  Gly  Val  Lys  Leu  Ser  Val  Pro  His  Ala  Asn  Asp  Leu  Gly  Leu
          355                      360                     365

Asp  Ala  Val  Thr  Leu  Gln  Tyr  Thr  Asp  Trp  Met  Asp  Asp  Asn  Asn  Gly
     370                      375                     380

Ile  Lys  Asn  Arg  Asp  Gly  Leu  Asp  Asp  Ile  Val  Gly  Asp  His  Asn  Val
385                      390                      395                           400

Ile  Cys  Pro  Leu  Met  His  Phe  Val  Asn  Lys  Tyr  Thr  Lys  Phe  Gly  Asn
               405                      410                          415

Gly  Thr  Tyr  Leu  Tyr  Phe  Phe  Asn  His  Arg  Ala  Ser  Asn  Leu  Val  Trp
               420                      425                     430

Pro  Glu  Trp  Met  Gly  Val  Ile  His  Gly  Tyr  Glu  Ile  Glu  Phe  Val  Phe
          435                      440                     445

Gly  Leu  Pro  Leu  Val  Lys  Glu  Leu  Asn  Tyr  Thr  Ala  Glu  Glu  Glu  Ala
     450                      455                     460

Leu  Ser  Arg  Arg  Ile  Met  His  Tyr  Trp  Ala  Thr  Phe  Ala  Lys  Thr  Gly
465                      470                      475                           480

Asn  Pro  Asn  Glu  Pro  His  Ser  Gln  Glu  Ser  Lys  Trp  Pro  Leu  Phe  Thr
               485                      490                          495
```

```
Thr  Lys  Glu  Gln  Lys  Phe  Ile  Asp  Leu  Asn  Thr  Glu  Pro  Met  Lys  Val
               500                      505                      510

His  Gln  Arg  Leu  Arg  Val  Gln  Met  Cys  Val  Phe  Trp  Asn  Gln  Phe  Leu
          515                      520                      525

Pro  Lys  Leu  Leu  Asn  Ala  Thr  Glu  Thr  Ile  Asp  Glu  Ala  Glu  Arg  Gln
     530                      535                      540

Trp  Lys  Thr  Glu  Phe  His  Arg  Trp  Ser  Ser  Tyr  Met  Met  His  Trp  Lys
545                           550                      555                     560

Asn  Gln  Phe  Asp  His  Tyr  Ser  Arg  His  Glu  Ser  Cys  Ala  Glu  Leu
                    565                      570                      575
```

( 2 ) INFORMATION FOR SEQ ID NO:2:

( i ) SEQUENCE CHARACTERISTICS:
      ( A ) LENGTH: 575 amino acids
      ( B ) TYPE: amino acid
      ( C ) STRANDEDNESS: single
      ( D ) TOPOLOGY: unknown ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:2:

```
Asp  Asp  His  Ser  Glu  Leu  Leu  Val  Asn  Thr  Lys  Ser  Gly  Lys  Val  Met
1                        5                       10                      15

Gly  Thr  Arg  Val  Pro  Val  Leu  Ser  Ser  His  Ile  Ser  Ala  Phe  Leu  Gly
               20                      25                      30

Ile  Pro  Phe  Ala  Glu  Pro  Pro  Val  Gly  Asn  Met  Arg  Phe  Arg  Arg  Pro
               35                      40                      45

Glu  Pro  Lys  Lys  Pro  Trp  Ser  Gly  Val  Trp  Asn  Ala  Ser  Thr  Tyr  Pro
     50                      55                      60

Asn  Asn  Cys  Gln  Gln  Tyr  Val  Asp  Glu  Gln  Phe  Pro  Gly  Phe  Ser  Gly
65                       70                      75                      80

Ser  Glu  Met  Trp  Asn  Pro  Asn  Arg  Glu  Met  Ser  Glu  Asp  Cys  Leu  Tyr
               85                      90                      95

Leu  Asn  Ile  Trp  Val  Pro  Ser  Pro  Arg  Pro  Lys  Ser  Thr  Thr  Val  Met
               100                     105                     110

Val  Trp  Ile  Tyr  Gly  Gly  Gly  Phe  Tyr  Ser  Gly  Ser  Ser  Thr  Leu  Asp
          115                     120                     125

Val  Tyr  Asn  Gly  Lys  Tyr  Leu  Ala  Tyr  Thr  Glu  Glu  Val  Val  Leu  Val
     130                     135                     140

Ser  Leu  Ser  Tyr  Arg  Val  Gly  Ala  Phe  Gly  Phe  Leu  Ala  Leu  His  Gly
145                      150                     155                     160

Ser  Gln  Glu  Ala  Pro  Gly  Asn  Val  Gly  Leu  Leu  Asp  Gln  Arg  Met  Ala
                    165                     170                     175

Leu  Gln  Trp  Val  His  Asp  Asn  Ile  Gln  Phe  Phe  Gly  Gly  Asp  Pro  Lys
               180                     185                     190

Thr  Val  Thr  Ile  Phe  Gly  Gln  Ser  Ala  Gly  Gly  Ala  Ser  Val  Gly  Met
               195                     200                     205

His  Ile  Leu  Ser  Pro  Gly  Ser  Arg  Asp  Leu  Phe  Arg  Arg  Ala  Ile  Leu
          210                     215                     220

Gln  Ser  Gly  Ser  Pro  Asn  Cys  Pro  Trp  Ala  Ser  Val  Ser  Val  Ala  Glu
225                      230                     235                     240
```

-continued

| | | | | | | | | | | | | | | |
|---|---|---|---|---|---|---|---|---|---|---|---|---|---|---|
| Gly | Arg | Arg | Arg | Ala 245 | Val | Glu | Leu | Gly | Arg 250 | Asn | Leu | Asn | Cys 255 | Asn | Leu |
| Asn | Ser | Asp | Glu 260 | Glu | Leu | Ile | His | Cys 265 | Leu | Arg | Glu | Lys | Lys 270 | Pro | Gln |
| Glu | Leu | Ile 275 | Asp | Val | Glu | Trp | Asn 280 | Val | Leu | Pro | Phe | Asp 285 | Ser | Ile | Phe |
| Arg | Phe 290 | Ser | Phe | Val | Pro | Val 295 | Ile | Asp | Gly | Glu | Phe 300 | Phe | Pro | Thr | Ser |
| Leu 305 | Glu | Ser | Met | Leu | Asn 310 | Ser | Gly | Asn | Phe | Lys 315 | Lys | Thr | Gln | Ile | Leu 320 |
| Leu | Gly | Val | Asn | Lys 325 | Asp | Glu | Gly | Ser | Phe 330 | Phe | Leu | Leu | Tyr | Gly 335 | Ala |
| Pro | Gly | Phe | Ser 340 | Lys | Asp | Ser | Glu | Ser 345 | Lys | Ile | Ser | Arg | Glu 350 | Asp | Phe |
| Met | Ser | Gly 355 | Val | Lys | Leu | Ser | Val 360 | Pro | His | Ala | Asn | Asp 365 | Leu | Gly | Leu |
| Asp | Ala 370 | Val | Thr | Leu | Gln | Tyr 375 | Thr | Asp | Trp | Met | Asp 380 | Asp | Asn | Asn | Gly |
| Ile 385 | Lys | Asn | Arg | Asp | Gly 390 | Leu | Asp | Asp | Ile | Val 395 | Gly | Asp | His | Asn | Val 400 |
| Ile | Cys | Pro | Leu | Met 405 | His | Phe | Val | Asn | Lys 410 | Tyr | Thr | Lys | Phe | Gly 415 | Asn |
| Gly | Thr | Tyr | Leu 420 | Tyr | Phe | Phe | Asn | His 425 | Arg | Ala | Ser | Asn | Leu 430 | Val | Trp |
| Pro | Glu | Trp 435 | Met | Gly | Val | Ile | His 440 | Gly | Tyr | Glu | Ile | Glu 445 | Phe | Val | Phe |
| Gly | Leu 450 | Pro | Leu | Val | Lys | Glu 455 | Leu | Asn | Tyr | Thr | Ala 460 | Glu | Glu | Glu | Ala |
| Leu 465 | Ser | Arg | Arg | Ile | Met 470 | His | Tyr | Trp | Ala | Thr 475 | Phe | Ala | Lys | Thr | Gly 480 |
| Asn | Pro | Asn | Glu | Pro 485 | His | Ser | Gln | Glu | Ser 490 | Lys | Trp | Pro | Leu | Phe 495 | Thr |
| Thr | Lys | Glu | Gln 500 | Lys | Phe | Ile | Asp | Leu 505 | Asn | Thr | Glu | Pro | Met 510 | Lys | Val |
| His | Gln | Arg 515 | Leu | Arg | Val | Gln | Met 520 | Cys | Val | Phe | Trp | Asn 525 | Gln | Phe | Leu |
| Pro | Lys 530 | Leu | Leu | Asn | Ala | Thr 535 | Glu | Thr | Ile | Asp | Glu 540 | Ala | Glu | Arg | Gln |
| Trp 545 | Lys | Thr | Glu | Phe | His 550 | Arg | Trp | Ser | Ser | Tyr 555 | Met | Met | His | Trp | Lys 560 |
| Asn | Gln | Phe | Asp | His 565 | Tyr | Ser | Arg | His | Glu 570 | Ser | Cys | Ala | Glu | Leu 575 | |